United States Patent
Infranca

[11] 3,931,817
[45] Jan. 13, 1976

[54] PEDIATRIC CORRECTIVE DEVICE

[76] Inventor: Leonard Infranca, 222 Front St., Mineola, N.Y. 11501

[22] Filed: Jan. 27, 1975

[21] Appl. No.: 544,410

[52] U.S. Cl. ............................................. 128/80 A
[51] Int. Cl.² ......................................... A61F 3/00
[58] Field of Search ..... 128/80 A, 80 R, 80 J, 80 B, 128/80 F, 83, 87

[56] References Cited
UNITED STATES PATENTS

| | | | |
|---|---|---|---|
| 2,702,542 | 2/1955 | Gessel | 128/80 A |
| 2,804,070 | 8/1957 | Faulkner | 128/80 A |
| 2,920,620 | 1/1960 | Rogers | 128/80 A |
| 3,109,424 | 11/1963 | Brachman | 128/80 A |
| 3,699,954 | 10/1972 | Craig | 128/80 A |
| 3,777,747 | 12/1973 | Freidman | 128/80 A |

*Primary Examiner*—Robert W. Michell
*Assistant Examiner*—J. Yasko
*Attorney, Agent, or Firm*—Bauer, Amer & King

[57] ABSTRACT

A pediatric device to control, within selected limits, the extent that a child can twist his feet. As an advance over known, generally similar devices, the traverse-limits are embodied on components which have intermeshing teeth. As a consequence, the teeth not only hold the components in relative positions, but very minute and accurate position adjustments can be made therebetween, by merely changing the teeth that establish the engagement. If desired, the positional change can be as small as the pitch of a single tooth.

4 Claims, 3 Drawing Figures

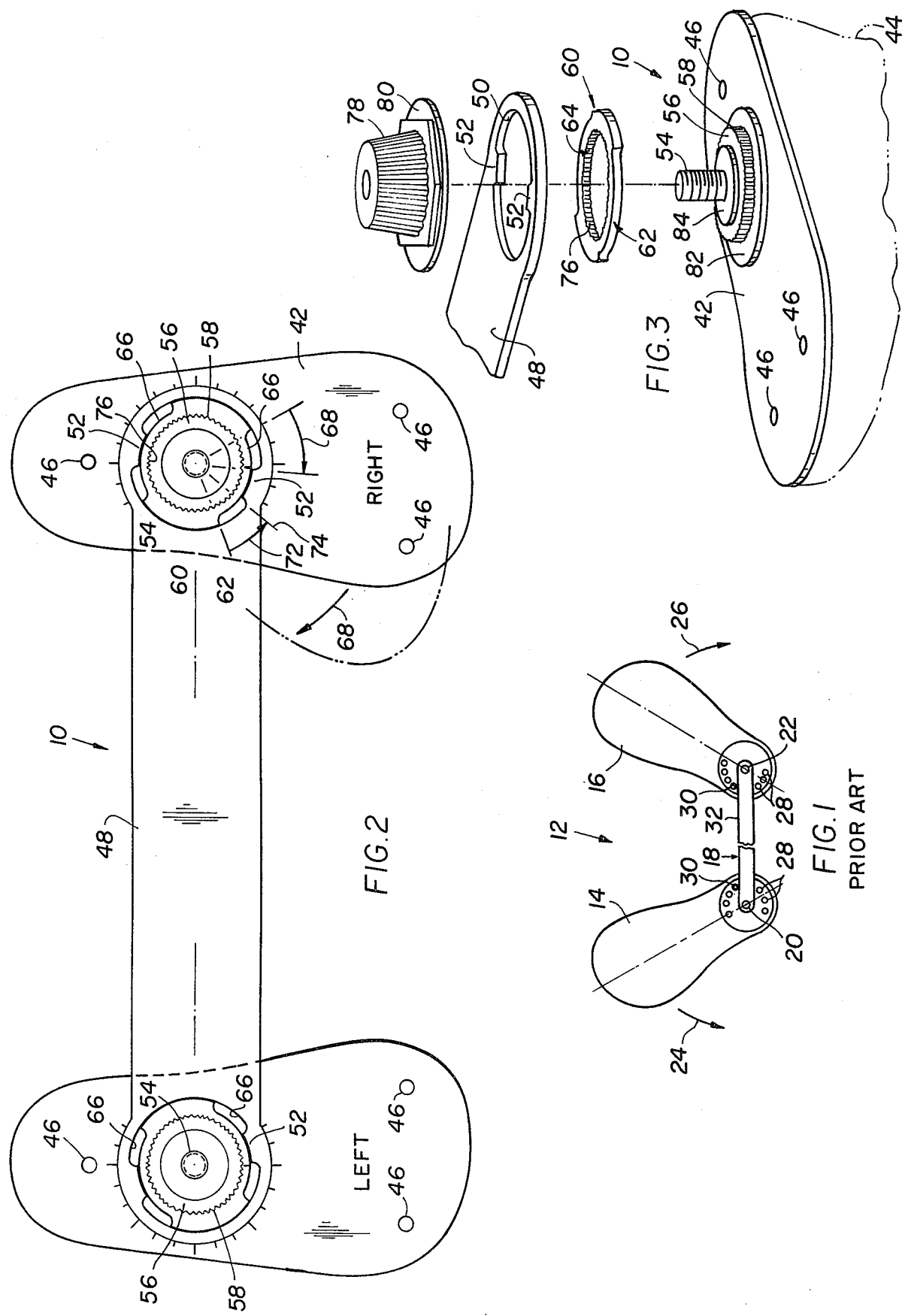

PEDIATRIC CORRECTIVE DEVICE

The present invention relates to movement-restraining pediatric devices, and more particularly to an improved pediatric device which, despite its simple construction, is sturdy and capable of a wide range of adjustment.

It is already well known in the patent literature, as exemplified by U.S. Pat. No. 3,109,424, how to use and construct a pediatric device to correct for abnormal toeing-in, i.e. internal tibial torsion, or toeing-out, i.e. external tibial torsion. This is also a primary use and objective of the within pediatric device. However, unlike known devices, the movement limits are not established merely by the abutment of a pin or the like against a stationary surface. This prior art technique, which characterizes presently known pediatric movement-restraining devices, is vulnerable to malfunction due to shearing of the stop pin, and also is not readily capable of minute adjustments. As to the latter, the stop pin is usually threadably disposed in a selected one, of a circumferential arrangement, of openings, and thus the smallest possible adjustment is limited to the smallest distance that can be left between adjacent openings.

Broadly, it is an object of the present invention to provide a pediatric corrective device with improved structural features overcoming the foregoing and other shortcomings of the prior art. Specifically, it is an object to distribute the force resisting movement by the patient beyond specified limits over the cumulative surface area of intermeshing teeth, thereby obviating any possibility of failure by shearing. Simultaneously, the intermeshing teeth permit minute and accurate adjustments in position, by as little as the pitch of a single tooth, if desired.

A construction in a pediatric corrective device demonstrating objects and advantages of the present invention includes a bar having an operative position connected in spanning relation between the patient's shoes. Said bar has adjacent each end an opening therein with a stop projection on a wall bounding said opening. There are also provided a plate for attachment to each said shoe, a threaded member extending perpendicularly of each said plate defining the axis for said permissible twisting traverses of said shoe, each said threaded member having an operative position projected centrally through one said end opening of said bar, a circular member fixedly mounted to each said plate at the base of said threaded member having teeth along its perimeter in encircling relation about said threaded member, and ring-like traverse-limiting members having inner and outer wall surfaces positionable in the clearance between each said circular member and said wall bounding said bar end opening. Each traverse-limiting member is provided with a traversing slot of a selected length in its outer wall surface for receiving the bar stop in projected position therein to thereby allow traversing movement until abutment by the bar stop with the opposite end walls bounding said traversing slot. Also, each traverse-limiting member has teeth along its inner wall surface to provide meshing engagement with the peripheral teeth of said circular member, whereby said meshing engagement holds the traversing slot in any selected traverse-limiting relation to the bar stop, and the same also enables the adjustments in relative positions of the slot and stop projection merely by changing the teeth that establish the meshing engagement.

The above brief description, as well as further objects, features and advantages of the present invention, will be more fully appreciated by reference to the following detailed description of a presently preferred, but nonetheless illustrative embodiment in accordance with the present invention, when taken in conjunction with the accompanying drawings, wherein:

FIG. 1 is an end elevational view of a prior art pediatric corrective device;

FIG. 2 is an end elevational view, on an enlarged scale, of the pediatric corrective device according to the present invention; and FIG. 3 is a perspective view showing the assembly of the connection of the pediatric device to the patient's shoe, and also further details of the structural features of said pediatric device.

Reference is now made to the drawings wherein the pediatric corrective device, generally designated 10, is illustrated in FIGS. 2 and 3. While there are devices available which generally achieve the same medical effect or objective as device 10, as exemplified by the prior art device 12 illustrated in FIG. 1, device 10 has many significant and noteworthy structural features that are not part of, or contemplated by, the prior art device 12. To better understand these differing features, it is helpful to understand the construction and mode of operation of device 12. Said device includes two shoe plates 14, 16 which are attached to the soles of the shoes of the patient. There is also included a bar 18 connected to each of the shoe plates, as at 20, 22, said connections functioning as axes for limited rotation of the shoe plates. That is, as already noted, assuming that a patient has internal tibial torsion or abnormally inwardly bent feet, device 12 is useful in holding his feet in an outwardly diverging relation as illustrated in FIG. 1, and also in permitting exercise movements in the corrective directions 24 and 26.

In the construction of the prior art device 12, however, and constituting specific aspects of the same which the device 10 hereof constitutes an improvement thereover, certain structural features are utilized to restrain the shoe plates 14 and 16 from permitting inturning of the patient's foot. These features include on each shoe plate a circumferential arrangement 28 of threaded openings, and the use of threaded pins or studs 30 as stops limiting the rotation of the shoe plates 14, 16. That is, as should be readily obvious from FIG. 1, to prevent turning of the shoe plates 14 and 16 towards each other and thus out of their outwardly diverging relation, the studs 30 are threaded into a cooperating opening 28 and prevent rotation of the shoe plates 14, 16 about the axes 20, 22 when they abut against the edge 32 of the bar 18. Among other shortcomings, this traverse-limiting means is not capable of minute adjustments since the spacing between the openings 28 cannot be reduced, for all practical purposes, to less than ¼ of an inch or the like. Also, the prohibited rotational traverses of the shoe plates 14 and 16, as achieved by the studs 30, result in extensive shear forces being placed on the studs 30, and thus over a period of time can ultimately result in shearing of one or both of these studs.

The improved pediatric corrective device 10, constructed as illustrated in FIGS. 2, 3, has significant operational advantages, one of which is that it is capable of very fine or minute adjustment. Device 10 similarly includes a pair of shoe plates 40 and 42 which in practice, as illustrated in FIG. 3, is attached to the soles of the child's shoes 44, using screws, rivets or the like at appropriate locations 46. Adapted to be connected in spanning relation between the shoe plates 40 and 42 is a correction bar 48. At each end of the bar 48, as best illustrated in FIG. 3, there is a generally circular opening 50 which has at least one, and could have, as illustrated, two opposing inwardly extending stop projections 52, the functioning of which will soon be apparent.

Referring now to FIG. 3, each shoe plate, as exemplified by shoe plate 42, includes a perpendicularly oriented threaded member 54 appropriately connected to the plate, as by welding or the like. Each threaded member 54 has a stationary circular base 56 which has teeth 58 appropriately machined in its peripheral end wall or surface. Thus, as best illustrated in FIG. 2, each member 56 thus presents circumferentially arranged teeth 58 in encircling relation about each of the threaded members 54.

Connection of the bar 48 in spanning relation between the shoe plates 40 and 42 contemplates assembling the bar openings 50 about each of the threaded members 54. Specifically, each of the openings 50 are placed about the smaller diameter member 56. This leaves clearance between the teeth 58 of member 56 and the wall which bounds the opening 50. In accordance with the present invention, positionable in this clearance is a ring-like traverse-limiting member 60. The ring-like body of each member 60 provides it with an outer surface 62 and an inner surface 64.

As may best be appreciated by reference specifically to shoe plate 42 in FIG. 2, there is provided in the outer surface 62 of each member 60 at least one, and possibly two, machined traversing slots 66. In the set-up illustrated in FIG. 2, it should be readily appreciated that shoe plate 42 can be rotated through a clockwise traverse 68 until there is abutment of an end wall bounding the traversing slot 66 with the stop 52, as at the reference location 70. Thus location 70 represents the holding position at which no further inward bending or twisting can occur for a patient suffering from tibial torsion.

Limited exercise movement in a counter-clockwise direction is possible during use of the device 10. Specifically, a counter-clockwise traverse 72 is possible until the opposite end wall of traversing slot 66 abuts against the opposite side of the stop 52, as at reference location 74. In the illustrated embodiment, the total traverse, i.e. the addition of the traverses 68 and 72, is approximately 30 degrees.

What has been described is capable of being achieved using the prior art corrective device 12. However, what cannot be achieved using device 12 is the minute adjustments that can be made in the reference locations 70 and 74 which limit the in-turning or out-turning of the patient's feet. To this end, each traverse-limiting member 60 has teeth 76 along its inner wall or surface 64 which matches in size and pitch that of the teeth 58 of the base member 56. Thus, when each member 60 is positioned in encircling relation about the base member 56, the cooperating teeth 76 and 58 achieve a meshing relationship. This meshing relationship, in an obvious manner, holds each member 60 in a position that prevents its rotative movement when there is abutment of the stop 52 against the end walls bounding the traversing slot 66. Also, adjustment at which abutment occurs, as exemplified by the locations 70 and 74, may be readily changed by advancing member 60 either clockwise or counter-clockwise relative to the stationary base member 56. This advancement can, of course, be made by as little as one tooth at a time if desired, although as a practical matter this small an adjustment is usually not required during treatment of the patient. An adjustment by two or three teeth is, however, often necessary and, of course readily made using the device 10.

Completing the construction of the assembled connection for the ends of the bar 48 and the shoe plates 40 and 42 is a nut 78 which threadably engages the upper portion of threaded member 54 which is exposed after assembly of member 60 and the end of bar 48 about the base member 56. Each nut 78 includes a disk 80 which serves as a closure for the opening 50 in that it is of sufficient diameter to extend in covering relation over the member 60 and thereby maintains this member in place. Washer 82 prevents rubbing contact between the shoe plates 42 and 40 with the bar 48 during pivotal traverses of the patient's feet. Similarly, washer 84 prevents rubbing contact between the closure disk 80 and the upper surface of the bar 48.

In the illustrated construction of the device 10, openings 50 were provided with two opposing stops 52 and the traverse-limiting member 60 with two cooperating opposing traversing slots 66. The use of these structural features in pairs makes it easier to complete and assemble the connection for the bar 48 with each of the shoe plates since the traversing slot is available for use whether the member 60 is in a "heads" or "tails" position. However, the within invention can be practiced without this convenience, in which instance only one stop 52 and only one traversing slot 66 would be provided.

A latitude of modification, change and substitution is intended in the foregoing disclosure, and in some instances some features of the invention will be employed without a corresponding use of other features. Accordingly, it is appropriate that the appended claims be construed broadly and in a manner consistent with the spirit and scope of the invention herein.

What is claimed is:

1. A pediatric corrective device adapted to be attached to the soles of a patient's shoes so as to confine twisting traverses of said patient's legs to within selected limits, said device comprising a bar having an operative position connected in spanning relation between said shoes and having adjacent each end an opening therein with a stop projection on a wall bounding each said opening, a plate for attachment to each said shoe, a threaded member extending perpendicularly of each said plate defining the axis for said permissible twisting traverses of said shoe, each said threaded member having an operative position projected centrally through one of said end openings, respectively of said bar, a circular member fixedly mounted to each said plate at the base of said threaded member having teeth along its perimeter in encircling relation about said threaded member, and ring-like traverse-limiting members having inner and outer wall surfaces positionable in the clearance between each said circular member and said wall bounding said bar end opening, each of said traverse-limiting members having at least one traversing slot of a selected length in said outer wall surface for receiving said stop projection in projected position therein to thereby allow traversing movement until abutment by said bar stop with the opposite end walls bounding said traversing slot, and teeth along said inner wall surface of said traverse-limiting member to provide meshing engagement with said peripheral teeth of said circular member, whereby said meshing engagement holds said traversing slot in any selected traverse-limiting relation to said bar stop and enables adjustments therein merely by changing said teeth that establish said meshing engagement.

2. A pediatric corrective device as claimed in claim 1 including a closure member adapted to threadably engage an exposed end of each said threaded member and of a circumferential size to extend in covering relation over said traverse-limiting member, to thereby hold each said traverse-limiting member in position.

3. A pediatric corrective device as claimed in claim 2 including a pair of traversing slots in each said traverse-limiting member in opposing relation to each other, and a cooperating pair of stop projections on said bar also in opposing relation to each other, to thereby facilitate the assembled connection of said bar with said plates.

4. A pediatric corrective device as claimed in claim 3 wherein the length of each said traversing slot is of an extent allowing a twisting traverse of approximately 30 degrees.

* * * * *